United States Patent [19]

Bolesky et al.

[11] Patent Number: 5,286,260
[45] Date of Patent: Feb. 15, 1994

[54] MODULAR HIP PROSTHESIS

[75] Inventors: Richard Bolesky; Todd S. Smith; Charles E. Whitcraft, Jr., all of Warsaw, Ind.

[73] Assignee: DePuy Inc., Warsaw, Ind.

[21] Appl. No.: 891,419

[22] Filed: May 29, 1992

Related U.S. Application Data

[60] Division of Ser. No. 450,058, Dec. 13, 1989, Pat. No. 5,181,928, which is a continuation of Ser. No. 896,857, Aug. 15, 1986, abandoned.

[51] Int. Cl.$^5$ ............................ A61F 2/36; A61F 2/32
[52] U.S. Cl. ........................................ 623/23; 623/18; 623/22
[58] Field of Search .................. 623/16, 18, 19, 20, 623/23

[56] References Cited

U.S. PATENT DOCUMENTS

| | | |
|---|---|---|
| 2,682,265 | 6/1954 | Collison . |
| 2,719,522 | 10/1955 | Hudack . |
| 2,765,787 | 10/1956 | Pellet . |
| 2,781,758 | 2/1957 | Chevalier . |
| 2,785,673 | 3/1957 | Anderson . |
| 3,064,645 | 11/1962 | Ficat et al. . |
| 3,067,740 | 12/1962 | Haboush . |
| 3,102,536 | 9/1963 | Rose et al. . |
| 3,806,957 | 4/1974 | Shersher . |
| 3,818,512 | 6/1974 | Shersher . |
| 3,863,273 | 2/1975 | Averill . |
| 3,918,441 | 11/1975 | Getscher . |
| 3,987,499 | 10/1976 | Scharbach et al. . |
| 4,051,559 | 10/1977 | Pifferi . |
| 4,115,875 | 9/1978 | Rambert et al. . |
| 4,404,691 | 9/1983 | Buning et al. . |
| 4,459,708 | 7/1984 | Buttazzoni . |
| 4,488,319 | 12/1984 | von Recûm . |
| 4,520,511 | 6/1985 | Gianezio et al. .......... 623/23 |
| 4,532,660 | 8/1985 | Field . |
| 4,578,081 | 3/1986 | Harder .................. 623/18 |
| 4,655,778 | 4/1987 | Koeneman . |
| 4,676,797 | 6/1987 | Anapliotis et al. ........ 623/18 |
| 4,698,063 | 10/1987 | Link et al. ............. 623/23 |
| 4,822,370 | 4/1989 | Schelhas . |
| 4,840,632 | 6/1989 | Kampner . |
| 4,842,606 | 6/1989 | Kranz et al. . |
| 4,865,605 | 9/1989 | Dines et al. . |
| 5,002,581 | 3/1991 | Paxson et al. . |

FOREIGN PATENT DOCUMENTS

| | | |
|---|---|---|
| 0163121A1 | 4/1985 | European Pat. Off. . |
| 0198163A2 | 2/1986 | European Pat. Off. . |
| 0190981A1 | 8/1986 | European Pat. Off. . |
| 2318396 | 10/1974 | Fed. Rep. of Germany ........ 623/18 |
| 3406358 | 12/1984 | Fed. Rep. of Germany ........ 623/18 |
| 3336005 | 4/1985 | Fed. Rep. of Germany ........ 623/18 |
| 1183230 | 12/1973 | France . |
| 2225141 | 8/1974 | France . |
| 2378505 | 7/1976 | France . |
| 2575383A | 12/1984 | France . |
| 2576793 | 1/1985 | France . |
| 1531487 | 11/1974 | United Kingdom . |
| 1443470 | 7/1976 | United Kingdom . |
| 1521679 | 8/1978 | United Kingdom . |
| 2070939 | 9/1981 | United Kingdom . |
| WO83/02555 | 8/1983 | World Int. Prop. O. . |

OTHER PUBLICATIONS

Tumorprotheses des Hüftgelenkes (Indikation und Ergebnisse); By: M. Jäger, L. Löffler, D. Kohn.

Concept and Material Properties of a Cementless hip Prosthesis System with Al$_2$O$_3$ Ceramic Ball Heads and Wrought Ti-6Al-4V Stems; By: K. Zweymüller and M. Semlitsch.

*Primary Examiner*—David Isabella
*Attorney, Agent, or Firm*—Barnes & Thornburg

[57] ABSTRACT

A modular hip prosthesis for the replacement of a portion of the femur is provided. The prosthesis is assembled from a kit that includes a stem member having an upper portion and a lower portion, with the lower portion sized to be received in the femur. The kit also includes a body member that is sized to replace a portion of the femur and is configured to be received over the upper portion of a stem member. The kit also includes a head member that is sized to replace the head of the femur. A neck member is provided to attach the head member to the body member to form an assembled prosthesis.

10 Claims, 3 Drawing Sheets

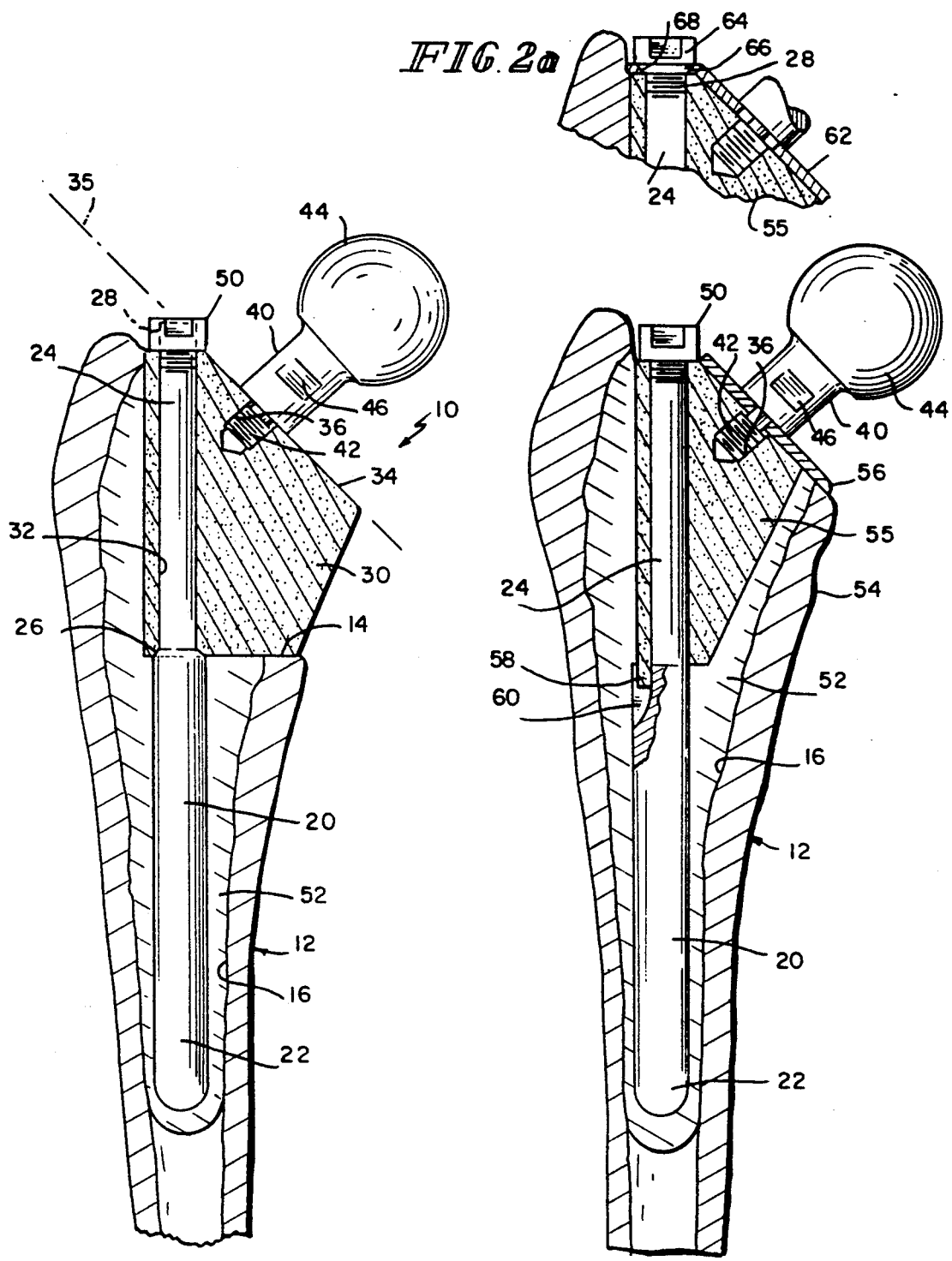

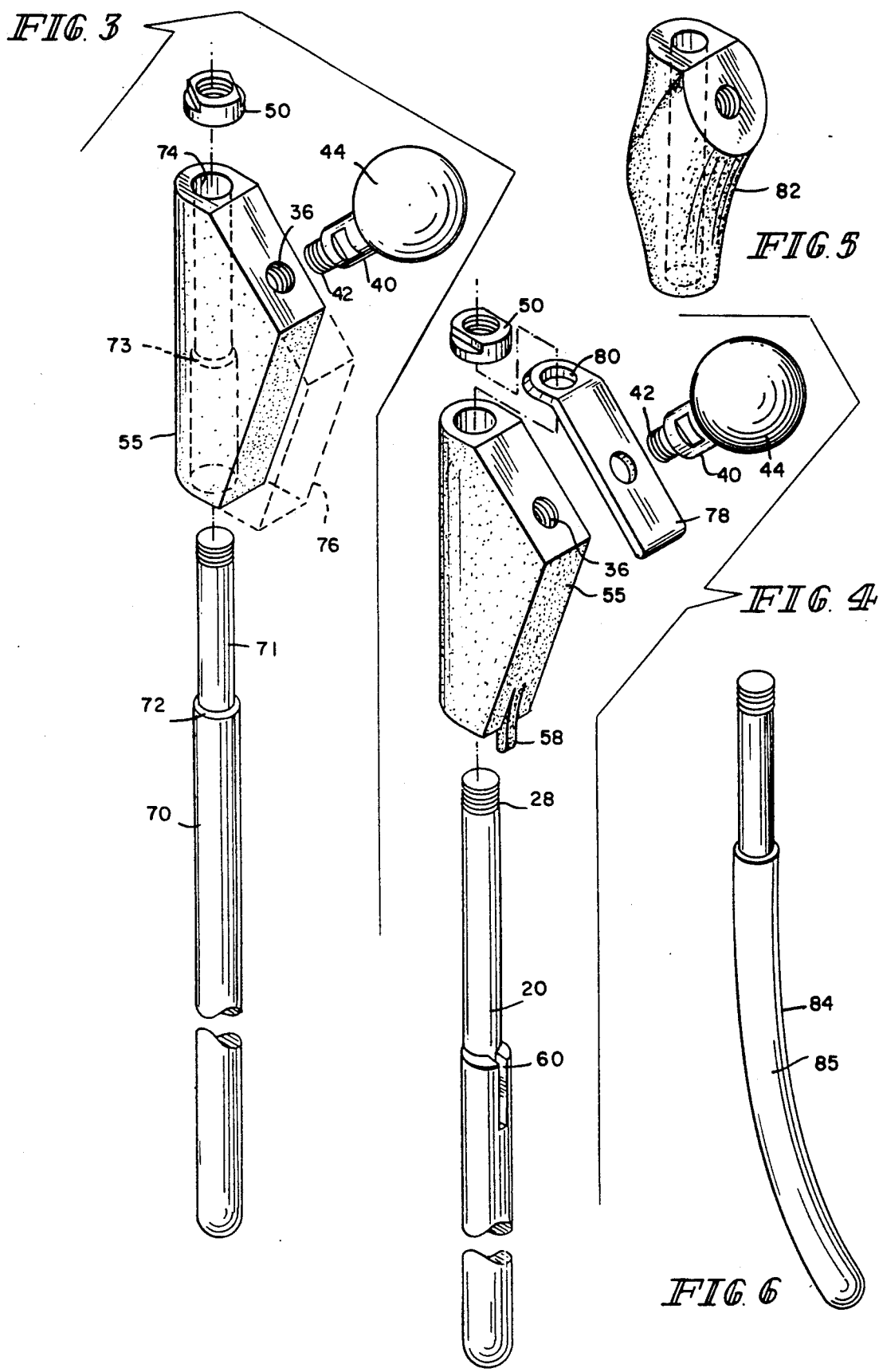

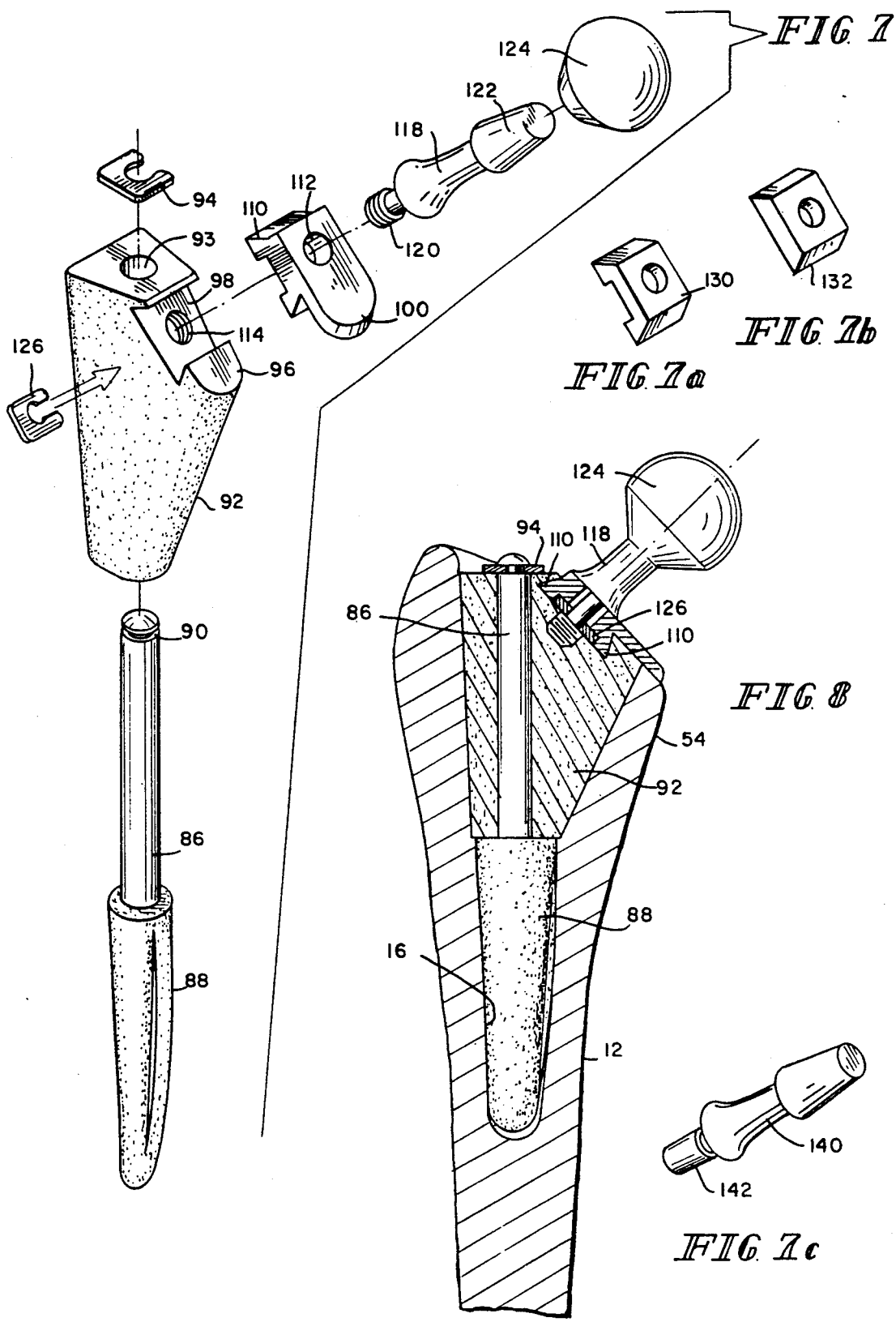

MODULAR HIP PROSTHESIS

This is a division of application Ser. No. 07/450,058 filed Dec. 13, 1989, now U.S. Pat. No. 5,181,928 which is a continuation of application Ser. No. 06/896,857 filed Aug. 15, 1986 (now abandoned).

BACKGROUND AND SUMMARY OF THE INVENTION

The present invention relates to prostheses for replacement of a portion of the hip joint. More particularly, the present invention relates to a modular prosthesis for replacement of the upper portion of the femur.

Conventional prostheses for the replacement of the upper portion of the femur are generally unitary structures. The conventional prosthesis generally includes a stem portion that is designed to extend downwardly into a cavity within the femur. The stem portion may be secured within the femur by the use of bone cement, or in other adaptations, the stem may be configured to promote bone ingrowth to secure the stem. The conventional hip prosthesis also includes a neck portion that is integral with the stem portion. The neck portion is configured to replace the neck of the femur which will normally be resected with the head of the femur. Integrally fixed to the neck portion will normally be a generally spherical head portion that is configured to replace the head of the femur. A collar may be provided between the neck portion and the stem portion to stabilize the prosthesis on the resected femur. Generally, the collar will rest upon the resected surface of the femur to disperse the load on the prosthesis over a greater area, and to compress the underlying bone. A collar may be provided between the neck portion and the stem portion to stabilize the prosthesis and function as a stop or reference point on the resected femur.

Because conventional prostheses are generally unitary devices, the practice has been to maintain a large inventory of prostheses of different sizes to accommodate the different bone sizes that are to be replaced. Generally, the patient is evaluated by x-ray or some other means to determine the approximate bone size, and consequently the approximate required prosthesis size. During the replacement operation, several different prostheses are made available as suggested by the evaluation. The appropriate prosthesis is then selected for insertion into the patient at the time of operation.

One problem with the conventional, unitary prosthesis is that the hospital has to maintain a large number of differently sized prostheses to accommodate different sizes of bones to be replaced. Generally, a supply of prostheses with and without a collar also must be maintained in the inventory. Also, prostheses with different shapes and angles of the stem and neck portion must be maintained. Even with this large inventory of prostheses, it is often difficult to find a prosthesis that is sized and shaped exactly for the individual patient.

Prostheses having a stem portion and a separate head portion are known. One such prosthesis is shown in U.S. Pat. No. 4,051,559. U.S. Pat. No. 4,051,559 discloses a prosthesis that includes a separate threaded stem portion that is adapted to be screwed into a prepared cavity within the femur. The prosthesis separately comprises a head portion that includes a neck and collar that is adapted to be mated with the stem portion. This prosthesis is not designed to be assembled prior to insertion within the patient. The stem portion must first be screwed into the cavity within the femur. The head portion is then attached to the installed stem portion by a bolt. The collar is designed to rest upon the resected surface of the femur to support the load placed on the prosthesis. Because of the design of the stem portion, the head portion must include the collar in order to support the weight that will be placed on the prosthesis. This prosthesis is limited in flexibility because the stem portion must be straight in order to be screwed into the femur. Also, the head portion, including the neck and collar is a unitary structure which further reduces the flexibility of the device.

Another prosthesis having a stem portion and a separate head portion is shown in U.S. Pat. No. 3,806,957. U.S. Pat. No. 3,806,957 discloses a prosthesis that includes a separate stem portion having a proximal end that is broadened somewhat. The broadened proximal end of the stem is configured to receive a head and threaded neck portion to form a complete prosthesis. The patent discloses that the neck may be elongated or shortened depending on the specific anatomy of different patients. This prosthesis, like the prosthesis disclosed in U.S. Pat. No. 4,051,559, is limited in flexibility because the head and neck portion is a unitary structure, and because the head and neck portion attaches directly into the stem portion.

A prosthesis in which the stem portion comprises more than one component is shown in U.S. Pat. No. 3,987,499. U.S. Pat. No. 3,987,499 discloses a prosthesis having a stem or shank component that includes two parts, an anchoring part and a transition part. A ball is connected to the transition part. Also, a collar may be included between the ball and a portion of the femur. The anchoring part is provided with external threads that are adapted to tap themselves into the femur. The transition part is coupled to the anchoring part by a guide pin and securing screw. The ball is adapted to be screwed onto the free end of the transition part. One problem with the prosthesis disclosed in U.S. Pat. No. 3,987,499 is that the prosthesis is designed to be placed in position within the body component by component, and assembled sequentially. Another problem with this prosthesis is that the neck is a part of the transition part, which reduces the flexibility of the device. In addition, the collar is configured to be supported only between the bone and the ball, and is thus subject to rotational and toggling instability.

One object of the present invention is to provide a modular hip prosthesis that has a great deal of flexibility in its assembly, both as to the size and shape of the assembled device.

Another object of the present invention is to provide a modular hip prosthesis that may be assembled in the operating room before any component is inserted into the patient.

Yet another object of the present invention is to provide a modular hip prosthesis that is configured to function with or without a collar.

Yet another object of the present invention is to provide a modular hip prosthesis that includes a stem portion that may be shaped to fit a curvature within the bone structure, if necessary.

According to the present invention, a kit for the assembly of a hip prosthesis for the replacement of a portion of a femur is provided. The kit comprises a stem member having an upper portion and a lower portion, with the lower portion sized to be received into the femur. The kit also comprises a body member that is sized to replace a portion of the femur and is configured to be received over the upper portion of the stem member. The kit also comprises a head member that is sized to replace the head of the femur, including means to attach the head member to the body member.

One feature of the present invention is that the kit preferably consists of stem members, body members, and head members, and attaching means all of various sizes and shapes. These separate components are adapted to be assembled together to form a custom prosthesis of a desired size and shape. One advantage of this feature is that a hip prosthesis of a desired size and shape may be assembled from the kit at the time of the operation.

Another feature of the present invention is that the kit comprises body members that are inserted over the stem members and are configured to bear a portion of the load that is exerted on the prosthesis. One advantage of this feature is that the prosthesis may be assembled without a collar component if the indications presented during the operation suggest that a collar may not be needed, or may produce unsatisfactory side effects.

In preferred embodiments of the present invention, the stem member, body member, and the head member are selected from a group consisting of differently sized and shaped members, respectively. One feature of the foregoing structure is that with different sizes and shapes of stem members, body members, and head members, the number of combinations available to assemble a hip prosthesis is greatly increased, without increasing the number of inventoried components. One advantage of this feature is that the flexibility of assembling a hip prosthesis for an individual patient is greatly increased.

Also in preferred embodiments of the present invention, the attaching means involves a neck member that is adapted to be rigidly attached to the body member and to the head member. The neck member is configured to replace the natural neck of the femur. The neck member, like the stem member, body member, and head member, is selected from a group consisting of differently sized neck members to increase the flexibility of the prosthesis.

The modular hip prosthesis of the present invention thus provides the ability to assemble a custom prosthesis by selecting different sizes and shapes of individual components to meet the requirements of the individual patient exactly. The provision of the kit concept for the prosthesis greatly reduces the inventory required to be maintained by the hospital. Also, the kit form of the prosthesis increases greatly the flexibility of the system, and provides for the assembly of a prosthesis that may otherwise be unavailable.

Additional objects, features, and advantages of the invention will be apparent to those skilled in the art upon consideration of the following detailed description of preferred embodiments exemplifying the best mode of carrying out the invention as presently perceived.

BRIEF DESCRIPTION OF THE DRAWINGS

The detailed description particularly refers to the accompanying figures in which:

FIG. 1 is a cross sectional view through one embodiment of the modular hip prosthesis of the present invention installed in a femur;

FIG. 2 is a view similar to FIG. 1 showing another embodiment of the present invention;

FIG. 2a is a partial view of a modification of the collar component and nut arrangement of the embodiment shown in FIG. 2;

FIG. 3 is an exploded perspective view of another embodiment of the present invention showing a modified stem member and body member;

FIG. 4 is a view similar to FIG. 3 showing another embodiment of the present invention with a collar component and an interlocking key and keyway in the body member and stem member;

FIG. 5 is a perspective view of another embodiment of the present invention showing a modified body member;

FIG. 6 is a perspective view of another embodiment of the present invention showing a modified stem member;

FIG. 7 is an exploded perspective view of another embodiment of the present invention showing a modified stem member and a modified neck and body member;

FIG. 7a is a perspective view of an adapter block for use when the collar component shown in FIG. 7 is not utilized;

FIG. 7b is a view similar to FIG. 7A showing a modified adapter block;

FIG. 7c is a perspective view of a modification of the neck member shown in FIG. 7; and FIG. 8 is a cross sectional view through the assembly illustrated in FIG. 7 installed in the femur.

DETAILED DESCRIPTION OF THE DRAWINGS

Referring now to FIG. 1, FIG. 1 shows a modular hip prosthesis 10 of the present invention inserted into a femur 12 in which the head and neck portions (not shown) have been resected. The resection of the head and neck portions of the femur 12 has been performed to leave a generally planar surface 14 on the femur 12. A cavity 16 has been formed in the femur 12 to receive the prosthesis 10. It will be understood that the resection procedure and the procedure for forming the cavity are well known in the art. It will also be understood that the cavity 16 may be formed to be the exact same size as the prosthesis 10, or if necessary, the cavity 16 may be formed to be somewhat larger than the size of the prosthesis 10. The cavity 16 shown in FIG. 1 is illustrative of the latter, with the cavity 16 being somewhat larger than the size of the prosthesis 10.

The prosthesis 10 includes an elongated stem member 20 that is generally circular in cross section and includes a lower portion 22 and an upper portion 24. The upper portion 24 has a diameter slightly less than the diameter of the lower portion 22. The demarcation between the upper portion 24 and the lower 22 is marked by a chamfer 26. The upper extremity of the stem member 20 terminates in a threaded end 28. The lower portion 22 may have any of several surface treatments, including, but not limited to, blasted, smooth, porous bonyingrowth, and coated.

A body member 30 is shown disposed over the upper portion 24 of the stem member 20, with the upper portion 24 extending through a bore 32 in the body member 30. The body member 30 includes an upwardly and inwardly (medially) facing surface 34 in which a threaded bore 36 has been formed. The surface 34 defines a plane 35 that is generally coincident with a plane defined by the base of the neck (not shown) that has been resected from the femur. The body member 30 may be formed by casting or machining and may have any of the several outer finishes discussed in connection with lower portion 22 of the stem member 20. It will be appreciated that, in the orthopedic implant art, having parts which can be made using machining techniques rather than casting techniques provides significant advantages.

A neck member 40 which replaces the natural neck of the femur (not shown) extends generally upwardly and inwardly from the surface 34. The neck member 40 includes a threaded projection 42 that engages the threaded bore 36 in the body member 30. A head member 44 is formed on the proximal end of the neck member 40, with the head member 44 replacing the natural head of the femur (not shown). Notches 46 are formed in the surface of the neck member to permit a wrench (not shown) to be used to tighten the neck member 40 into the body member 30.

The prosthesis 10 is assembled by first inserting the upper portion 24 of the stem member 20 through the bore 32 in the body member 30. A nut 50 is then engaged with the threaded end 28 of the stem member 20 to secure the stem member 20 to the body member 30. It will be understood that the distal end of the bore 32 in the body member 30 includes a chamfer to mate with the chamfer 26 on the stem member 20 to provide a secure engagement. The neck member 40 is then installed in the body member 30 by engaging the threaded projection 42 with the threaded bore 36. The neck member 40 is then tightened using a wrench (not shown) in the notches 46.

To install the assembled prosthesis 10 in the femur 12, a grouting material 52, or bone cement material, is first injected into the cavity 16. The prosthesis 10 is then placed in the cavity 16 such that the distal end of the body member 30 rests upon the surface 14, and the lower portion 22 of a stem member 20 extends downwardly into the cavity 16. The grouting material 52 surrounds the lower portion 22 of the stem 20 and in some cases a portion of the body member 30 and acts in a known manner to secure the prosthesis 10 within the femur 12.

FIG. 2 shows another embodiment of the present invention that is configured to fulfill slightly different anatomical requirements that may be indicated during the replacement procedure. This embodiment is configured to replace a portion of the femur 12 in which only the head and neck portions (not shown) have been resected. The Calcar portion 54 of the femur 12 has been left intact. Therefore, a smaller body member 55 is shown that can be disposed totally within the cavity 16 in the femur 12. Also, a collar 56 is provided that mates with the body member 55 and extends over the Calcar portion 54 of the femur 12. The collar 56 is provided to distribute the load between the body member 55 and the Calcar portion 54. In this embodiment, the body member 55 includes a key 58 that is received in a keyway 60 that is formed in the stem 20. The key 58 and keyway 60 cooperate to prevent any rotation of the body member 55 with respect to the stem member 20. The prosthesis 10 shown in FIG. 2 is inserted into the cavity 16 of the femur 12 that has been filled with a grouting material 52 to secure the prosthesis 10 in a known manner.

FIG. 2a shows a modification of the embodiment shown in FIG. 2. Specifically, the collar 56 of FIG. 2 is replaced by a collar 62 that extends over the threaded end 28 of the stem member 20. A chamfered hole 66 is formed in the extension of the collar 62 that receives the threaded end 28 of the stem member 20. A nut 64 with a chamfer 68 is provided to engage the threaded end 28 of the stem member 20 with the chamfer 68 of the nut engaging the chamfered hole 66 of the collar 62. The chamfer 68, 66 cooperate to securely engage the collar 62 between the body member 55 and the nut 64.

FIG. 3 shows another embodiment of the present invention including a slightly modified stem member 70 that engages the body member 55 of the embodiment shown in FIG. 2. Specifically, the stem member 70 includes a shorter upper portion 71 in comparison to the stem member 20. A chamfer 72 is provided between the upper portion 71 and the main portion of the stem member 70. The body member 55 includes a modified bore 74 extending therethrough to receive the stem member 70. The modified bore 74 has a chamfer 73 to mate with the chamfer 72 on the stem member 70. This modified stem member 70 and body member 55 may be used when additional strength in the stem member 70 is required, such as, for example, when the stem member 70 has a diameter smaller than normal. FIG. 3 also shows an extension 76 (shown only in dotted) that may be added to the body member 55 to make the body member 55 similar to the body member 30 shown in FIG. 1. The extension 76 will be required if the Calcar portion 54 (FIG. 2) of the femur 12 is being resected and replaced.

FIG. 4 shows another embodiment of the present invention similar to the embodiment shown in FIGS. 2 and 2a. In the embodiment shown in FIG. 4, the key 58 on the body portion 55 and the keyway 60 on the stem member 20 are located on the opposite side compared to the embodiment shown in FIG. 2. Also, the collar 78 is similar to the collar 62 shown in FIG. 2a, however the hole 80 in the extension does not contain a chamfer, thereby permitting the use of the unchamfered nut 50 to engage the threaded end 28 of the stem member 20.

FIG. 5 shows another embodiment of the present invention in which a body member 82 is formed in a somewhat irregular shape. The irregular shaped body 82 may be preferable for insertion into certain femurs (not shown). It will be understood that the body member 82 may be a cast material, or may be machined in a known manner and may have a surface treatment similar to that described in relation to the body member 30 (FIG. 1).

FIG. 6 shows another embodiment of the present invention having a modified stem member 84. Specifically, the stem member 84 includes a curved lower portion 85 that may be inserted into the cavity 16 in the femur 12 (not shown) when the anatomical indications so dictate. It will be understood that the stem member 84 may be mated with either the body member 30, the body member 55, or the body member 82, as discussed previously.

FIG. 7 shows yet another embodiment of the present invention. In this embodiment, a stem member 86 is provided that includes a lower portion 88 that is coated with a bone-ingrowth porous metal coating. Bone-ingrowth coatings are known in the art, and it will be understood that this type of stem 86 is adapted to be inserted into a bone without the use of any grouting or cement material. The upper end of the stem 86 includes a groove 90 that is adapted to mate With a stem clip 94 after the stem member 86 has been inserted through a bore 93 in the body member 92. It will be understood that the groove 90 and the stem clip 94 function in a manner similar to the threaded end 28 and nuts 50, 64 shown in FIGS. 1-3 to secure the stem member 86 within the body member 92. The body member 92 includes a generally upwardly and inwardly (medially) facing surface 96 that is formed to include a generally trapezoid-shaped slot 98. A collar 100 is provided that includes a generally trapezoidal-shaped projection 110 that is configured to dovetail into the slot 98 to align and position the collar 100 in the body member 92. The collar 100 includes a hole 112 formed therethrough that aligns with a threaded hole 114 in the body member 92 when the collar 100 is mated with the body member 92.

FIG. 7 also shows a modified neck member 118 that includes a threaded end 120 and a tapered end 122. The neck member 118 is secured to the body member 92 by passing the threaded end 120 through the hole 112 in the collar 100 and into the threaded hole 114. A separate head member 124 is shown that is formed to include a tapered hole (not shown) that mates with the tapered end 122 of the neck member 118 to secure the head member 124 to the neck member 118. It will be understood that the neck member 118 and the head member 124 can be of various shapes and sizes other than those illustrated in FIG. 7. A collar clip 126 is shown that inserts under the projection 110 of the collar 100 to lock the neck member 118 in position after it has been screwed into the threaded hole 114 in the body member 92.

FIG. 7a shows an adapter block 130 that may be inserted into the slot 98 if the collar 100 (FIG. 7) is not used. The adapter block 130 is sized to fill the slot 98 so that the surface 96 on the body member 92 will be generally planar. The adapter block 130 shown in FIG. 7a is configured to accept the stem clip 126 as described above.

FIG. 7b shows another adapter block 132 that also may be inserted into the slot 98 if the collar 100 (FIG. 7) is not used. The adapter block 132 is sized to fill the slot 98 so that the surface 96 on the body member 92 will be generally planar. The adapter block 132 differs from the adapter block 130 in that block 132 is used when no stem clip 126 will be utilized.

FIG. 7c shows a modified neck member 140 that is similar to the neck member 118 shown in FIG. 7. Neck member 140 differs in that the threaded end 120 (FIG. 7) is replaced by a tapered end 142 that may be inserted into a tapered hole (not shown) in any of the body members, such as body member 92 (FIG. 7).

FIG. 8 shows the prosthesis of FIG. 7 assembled and in a use position. To assemble the embodiment shown in FIG. 7, the stem member 86 is first inserted through the bore 93 in the body member 92. The stem clip 94 is then engaged with the groove 90 to secure the stem member 86 within the body member 92. The collar 100 is then engaged with the body member 92 by sliding the projection 110 into the slot 98 so that the hole 112 aligns with the threaded hole 114. The neck member 118 is then threadingly engaged into the threaded hole 114 by the threaded end 120. After the neck member 118 is tightened, the collar clip 126 is inserted under the projection 110 to lock the neck member 118 in position. The head member 124 is then inserted over the tapered end 122 of the neck member 118 to secure the head member 124 to the neck member 118.

The assembled prosthesis is then inserted into the cavity 16 of the femur 12 so that the collar 100 extends over the Calcar portion 54. It will be understood that in this embodiment the cavity 16 is excavated only to the extent necessary to permit the assembled prosthesis to exactly fit within the cavity 16. As discussed previously, the lower portion 88 of the stem member 86 will be secured within the femur 12 by the natural growth process of the bone into the porous surface. Illustratively, the body member 92 may also be coated with a bone-ingrowth material to enhance this ingrowth process.

Although specific embodiments have been shown assembled in FIGS. 1-8, it will be understood that the components shown in the figures may be interchangeable, and a prosthesis may be assembled utilizing combinations of the illustrated components. This ability to select different sizes and shapes of components to assemble a prosthesis greatly enhances the flexibility available at the time of the operation. Thus, depending upon the anatomical indications presented by the patient, numerous combinations are available to assemble a prosthesis at the time of the operation to meet the exact requirements for that patient.

Although the invention has been described in detail with reference to preferred embodiments and specific examples, variations and modifications exist within the scope and spirit of the invention as described and defined in the following claims.

What is claimed is:

1. A modular hip prosthesis assembly for the replacement of a portion of a femur, the assembly comprising
   a stem member of a predetermined size and shape having an upper portion and a lower portion and selected from a group consisting of differently sized and shaped stem members, each of said stem members lower portions sized and shaped to be received into said femur,
   a body member of a predetermined size and shape to replace a portion of the femur and selected from a group consisting of differently sized and shaped body members, each of said body members configured to be received over one of said upper portions of said stem members,
   a head member of a predetermined size and shape to replace the head of the femur and selected from a group consisting of differently sized and shaped head members, and
   a neck member of a predetermined size and shape selected from a group consisting of differently sized and shaped neck members demountably engageable with any one of said body members and adapted to receive one of said head members in a spaced apart relation from one of said body members.

2. The assembly of claim 1, further comprising a collar member of a predetermined size and shape selected from a group consisting of differently sized and shaped collar members and adapted to be interposed between one of said body members and one of said neck members.

3. The assembly of claim ,1 wherein said one neck member includes a first end for engaging said one of said head members and a second end for engaging said one of said body members, and wherein said first end is formed to include a tapered projection that is sized to be received into a tapered hole in said one of said head members to secure said one of said head members to said one of said neck members.

4. The assembly of claim 3, wherein said second end is formed to include a tapered projection that is sized to be received into a tapered hole in said one of said body members to secure said one of said neck members to said one of said body members.

5. A kit for the assembly of a hip prosthesis for the replacement of a head, neck, and adjacent portions of a femur, the neck of the femur having a base defining a neck basal plane, the kit comprising at least one stem member having a predetermined shape and size to be inserted into the shaft of the femur, said stem member selected from a group consisting of differently sized and shaped stem members, said group of stem members having generally uniformly sized upper portions, at least one body member adapted to mate with said stem member and having a predetermined shape and size to replace a portion of the femur and to define a plane generally coincident with said neck basal plane, said body member selected from a group consisting of differently sized and shaped body members, each body member in said group of body members formed to include a generally uniformly sized bore adapted to receive said upper portion of one of said stem members at least one neck member adapted to mate with said body member and having a predetermined shape and size, said neck member selected from a group consisting of differently sized and shaped neck members, and at least one head member adapted to mate with said neck member and having a predetermined shape and size to replace the head portion of the femur, said head member selected from a group consisting of differently sized and shaped head members.

6. A modular hip prosthesis assembly for the replacement of a portion of a femur, the assembly comprising a stem member of a predetermined size and shape having an upper portion and a lower portion and selected form a group consisting of differently sized and shaped stem members, each of said stem members lower portions sized and shaped to be received into said femur, a body member of a predetermined size and shape to replace a portion of the femur and selected from a group consisting of differently sized and shaped body members, each of said body members configured to be attached to one of said upper portions of said stem members, a head member of a predetermined size and shape to replace the head of the femur and selected from a group consisting of differently sized and shaped head members, and a neck member of a predetermined size and shape selected from a group consisting of differently sized and shaped neck members demountably engageable with any one of said body members and configured to be attached to one of said head members in a spaced apart relation from one of said body members.

7. The assembly of claim 6, further comprising a collar member of a predetermined size and shape selected form a group consisting of differently sized and shaped collar members and configured to be interposed between one of said body members and one of said neck members.

8. The assembly of claim 6, wherein said one neck member includes a first end for engaging said one of said head members and a second end for engaging said one of said body members, and wherein one of said first ends of said neck member and said one head member is formed to include a tapered portion that is located thereon and is sized to be received into a tapered hole located in the other of said one end of said neck member and said one head member, respectively, to secure said one of said head members to said one of said neck members.

9. The assembly of claim 8, wherein one of said second end and said body members, respectively, is formed to include a tapered projection that is sized to be received into a tapered hole in the other one of said second end and one of said body members to secure said one of said neck members to said one of said body members.

10. A kit for the assembly of a hip prosthesis for the replacement of a head, neck, and adjacent portions of a femur, the neck of the femur having a base defining a neck basal plane, the kit comprising at least one stem member having a predetermined shape and size to be inserted into the shaft of the femur, said stem member selected from a group consisting of differently sized and shaped stem members, said group of stem members having generally uniformly sized upper portions, at least one body member adapted to mate with said stem member and having a predetermined shape and size to replace a portion of the femur and to define a plane generally coincident with said neck basal plane, said body member selected from a group consisting of differently sized and shaped body members, each body member in said group of body members formed to include an attachment portion for securement with said upper portion of one of said stem member, at least one neck member adapted to mate with said body member and having a predetermined shape and size, said neck number selected form a group consisting of differently sized and shaped neck members, and at least one head member adapted to mate with said neck member and having a predetermined shape and size to replace the head portion of the femur, said head member selected from a group consisting of differently sized and shaped head members.

* * * * *